United States Patent [19]
Kalbe et al.

[11] Patent Number: 6,025,357
[45] Date of Patent: Feb. 15, 2000

[54] ANTHELMINTIC PASTE

[75] Inventors: Jochen Kalbe, Leichlingen; Helmut Schnabel, Odenthal, both of Germany

[73] Assignee: Bayer Aktiengesellschaft, Leverkusen, Germany

[21] Appl. No.: 09/101,931

[22] PCT Filed: Jan. 3, 1997

[86] PCT No.: PCT/EP97/00006

§ 371 Date: Jul. 13, 1998

§ 102(e) Date: Jul. 13, 1998

[87] PCT Pub. No.: WO97/25976

PCT Pub. Date: Jul. 24, 1997

[30] Foreign Application Priority Data

Jan. 16, 1996 [DE] Germany ............ 196 01 263

[51] Int. Cl.⁷ .......... A61K 31/495; A61K 31/47
[52] U.S. Cl. .......... 514/250; 514/25.5; 514/307
[58] Field of Search ............ 514/250, 255, 514/307

[56] References Cited

U.S. PATENT DOCUMENTS

| | | | |
|---|---|---|---|
| 4,117,156 | 9/1978 | Loewe et al. | 424/302 |
| 4,447,414 | 5/1984 | Gay et al. | 424/250 |
| 4,675,174 | 6/1987 | Eckenhoff | 424/15 |
| 5,036,069 | 7/1991 | Andrews et al. | 514/249 |
| 5,824,653 | 10/1998 | Beuvry et al. | 514/30 |

FOREIGN PATENT DOCUMENTS

| | | |
|---|---|---|
| 279343 | 8/1988 | European Pat. Off. . |
| 685370 | 6/1995 | Switzerland . |

*Primary Examiner*—Kevin E. Weddington
*Attorney, Agent, or Firm*—Joseph C. Gil; Godfried R. Akorli

[57] ABSTRACT

The present invention relates to hexahydropyrazino-derivative-based anthelmintic pastes for horses, dogs and cats, which are characterized in that they comprise corn starch and glycerol in addition to the active compound.

2 Claims, No Drawings

ANTHELMINTIC PASTE

The present invention relates to hexahydropyrazino-derivative-based anthelmintic pastes for horses, dogs and cats.

Pastes comprising praziquantel have been disclosed in EP-A 279 343. However, the disadvantage of these pastes is their high water content. The pastes must therefore be protected from attack by pathogenic bacteria by means of preservatives. Also, homogeneous admixture of the active compounds, which are sparingly soluble in water, frequently causes problems.

The present invention relates to hexahydropyrazino-derivative-based anthelmintic pastes for horses, dogs and cats which are characterized in that they comprise corn starch and glycerol as adjuvants for paste formation, in addition to the active compound.

This formulation
1. is composed of only a few components,
2. is composed of inexpensive components,
3. manages without particular preservatives and
4. is easy to prepare.

Preferred mixtures according to the invention are those which comprise praziquantel and epsiprantel as hexahydropyrazino derivatives. Praziquantel is especially preferred.

The formulations according to the invention comprise the active compound in weight concentrations of 5 to 30%, preferably 10 to 20%.

The formulations according to the invention comprise corn starch in weight concentrations of 10 to 30%, preferably 15 to 25%.

The formulations according to the invention comprise glycerol in weight concentrations of 40 to 80%, preferably 55 to 75%. The individual components add up to 100%. The ratio of corn starch to glycerol is chosen in such a way that a formulation results which is easy to process, to package and to use.

In addition to the hexahydropyrazinones, the formulations according to the invention can also comprise further active compounds. These are phenylguanidines, benzimidazoles or tetrahydropyrimidines.

Phenylguanidines which may be mentioned are those of the formula (I):

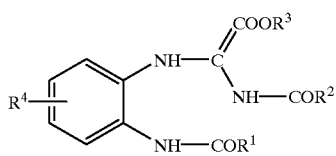

(I)

in which
$R_1$ represents hydrogen, optionally substituted alkyl, cycloalkyl, alkoxy, aryl or amino,
$R^2$ represents hydrogen, optionally substituted alkyl, cycloalkyl, alkenyl, alkinyl, aryl, alkoxy or alkenoxy,
$R^3$ represents hydrogen, optionally substituted alkyl, cycloalkyl, alkenyl, alkinyl or aryl and
$R^4$ represents alkyl, alkoxy, phenoxy, alkylthio, phenylthio, phenylsulphinyl, phenylsulphonyl or benzoyl which are optionally substituted by halogen, alkoxy, alkylthio, halogenoalkoxy or halogenoalkylthio.

Benzimidazoles which may be mentioned are those of the formula (II):

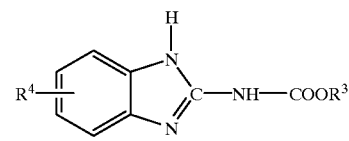

(II)

in which $R^3$ and $R^4$ have the meanings given for the compounds of the formula (I).

Tetrahydropyrimidines which may be mentioned are those of the formula (III):

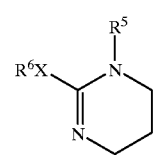

(III)

in which
$R^5$ represents hydrogen or alkyl,
$R^6$ represents optionally substituted phenyl or thienyl and
X represents —$(CH_2)_{2-3}$— or —CH═CH—.

The phenylguanidines include, for example, febantel and netobimine.

The benzimidazoles are, for example, febendazole, albendazole, oxibendazole, oxfendazole, mebendazole, flubendazole, parbendazole and luxabendazole.

The tetrahydropyrimidines include, for example, pyrantel, morantel and oxantel.

The pastes according to the invention are suitable for controlling pathogenic endoparasites encountered in horses in animal keeping and livestock breeding; they have a favourable toxicity to warm-blooded species. They are effective against all or individual developmental stages of the pests and against resistant and normally sensitive species. The pathogenic endoparasites include Cestodes, Trematodes, Nematodes and Acanthocephala, in particular:

From the order of the Pseudophyllidea, for example: Diphyllobothrium spp., Spirometra spp., Schistocephalus spp.

From the order of the Cyclophyllidea, for example: Mesocestoides spp., Anoplocephala spp., Paranoplocephala spp., Moniezia spp., Taenia spp., Echinococcus spp., Hydatigera spp., Diorchis spp., Dipylidium spp., Joyeuxiella spp., Spyrometra spp.

From the subclass of the Digenea, for example: Schistosoma spp., Fasciola spp., Dicrocoelium spp., Opisthorchis spp.

From the order of the Enoplida, for example: Trichuris spp., Capillaria spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Poteriostomum spp., Cyclicocyclus spp., Stephanurus spp., Ancyclostoma spp., Uncinaria spp., Cyathostomum spp., Metastrongylus spp., Dictyocaulus spp., Muellerius spp., Protostrongylus spp., Elaphostrongylus spp., Parelaphostrongylus spp., Crenosoma spp., Paracrenosoma spp., Filaroides spp., Parafilaroides spp., Marshallagia spp., Hyostrongylus spp., Ollulanus spp., Craterostomum spp., Cyclicodontophorus spp., Hyalocephalus spp., Cylindropharynx spp., Caballonema spp., Elaeophorus spp., Dirofilaria spp., Onchocerca spp., Setaria spp.

From the order of the Oxyurida, for example: Oxyuris spp., Enterobius spp.

From the order of the Ascaridia, for example: Ascaris spp., Toxascaris spp., Toxocara spp., Parascaris spp., Probstmangria spp.

From the order of the Spirurida, for example: Thelazia spp., Habronema spp., Draschia spp., Dracunculus spp.

The product can be administered both prophylactically and therapeutically.

The preferred use concentration of the mixture according to the invention is 1 to 300 mg, preferably 5 to 50 mg, of hexahydropyrazine per kg of live weight.

Further anthelmintic active compounds can be added for use at a rate of application of 0.1 to 20 mg, preferably 1 to 10 mg, especially preferably approx. 5 mg, per kg.

EXAMPLE 1

Paste for oral administration or for admixing to the feed
Composition:

Praziquantel 20.0 g

Corn starch 15.0 g

Glycerol 65.0 g

Preparation:

The components are stirred together. This gives a paste with which suitable applicators can be filled.

We claim:

1. Hexahydropyrazino-derivative-based anthelmintic pastes for horses, dogs and cats, which are characterized in that they comprise corn starch and glycerol as adjuvants for paste formation, in addition to the active compound.

2. Anthelmintic pastes for horses, dogs and cats according to claim 1, characterized in that they comprise the Hexahydropyrazino-derivative in weight concentrations of 5 to 30%, corn starch in weight concentrations of 10 to 30% and glycerol in weight concentrations of 40 to 80%.

* * * * *